(12) United States Patent
Thathagar et al.

(10) Patent No.: US 9,550,797 B2
(45) Date of Patent: Jan. 24, 2017

(54) PREPARATION OF GRIGNARD REAGENTS USING A FLUIDIZED BED

(71) Applicant: DPX Holdings B.V., Amsterdam (NL)

(72) Inventors: Mehul Thathagar, Echt (NL); Peter Poechlauer, Echt (NL); Rafael Wilhelmus Elisabeth Ghislain Reintjens, Echt (NL); Michel Goldbach, Echt (NL)

(73) Assignee: Patheon Holdings I B.V., Amsterdam (NL)

( * ) Notice: Subject to any disclaimer, the term of this patent is extended or adjusted under 35 U.S.C. 154(b) by 0 days.

(21) Appl. No.: 14/899,445

(22) PCT Filed: Jun. 27, 2014

(86) PCT No.: PCT/EP2014/063704
§ 371 (c)(1),
(2) Date: Dec. 17, 2015

(87) PCT Pub. No.: WO2014/207206
PCT Pub. Date: Dec. 31, 2014

(65) Prior Publication Data
US 2016/0137669 A1    May 19, 2016

(30) Foreign Application Priority Data
Jun. 27, 2013    (EP) .................................... 13173979

(51) Int. Cl.
*C07F 3/02*    (2006.01)
*C07D 257/02*    (2006.01)
(Continued)

(52) U.S. Cl.
CPC ................. *C07F 3/02* (2013.01); *C07C 29/40* (2013.01); *C07C 67/30* (2013.01); *C07D 257/02* (2013.01); *C07F 15/0046* (2013.01)

(58) Field of Classification Search
CPC ............. C07F 3/02; C07C 29/40; C07C 37/00
See application file for complete search history.

(56) References Cited

U.S. PATENT DOCUMENTS 2,464,685 A    3/1949    Hirsch
3,911,037 A    10/1975    Blackmar et al.
(Continued)

FOREIGN PATENT DOCUMENTS

DE    1293767 B    4/1969
WO    WO01/85329 A2    11/2001
WO    WO 2013/121443    *    8/2013    ........... C07C 231/22

OTHER PUBLICATIONS

International Preliminary Report on Patentability and the Written Opinion dated Jan. 7, 2016 from international parent application PCT/EP2014/063704 filed on Jun. 27, 2014.
(Continued)

*Primary Examiner* — Yate K Cutliff
(74) *Attorney, Agent, or Firm* — Pierce Atwood LLP; Raymond G. Arner

(57) ABSTRACT

The present invention relates to a process of preparing a Grignard reagent comprising reacting magnesium particulates in a fluid bed reactor. The present invention further relates to a continuous process comprising fluidizing magnesium particulates in a reactor, forming the Grignard reagent continuously, and reacting the Grignard reagent with a substrate.

38 Claims, 5 Drawing Sheets

(51) Int. Cl.
*C07F 15/00* (2006.01)
*C07C 29/40* (2006.01)
*C07C 67/30* (2006.01)

(56) References Cited

U.S. PATENT DOCUMENTS

| | | | |
|---|---|---|---|
| 4,105,703 A | | 8/1978 | Motta |
| 5,559,111 A | * | 9/1996 | G oschke ............... C07C 229/36 514/227.5 |
| 7,009,078 B1 | * | 3/2006 | Herold .................... C07C 51/06 564/161 |

OTHER PUBLICATIONS

Jimeno et al., Fentanyl and Its Analogue N-(1-Phenylpyrazol-3-yl)-N-[1-(2-phenylethyl)-4-piperidyl]propanamide: 1H- and 13C-NMR Spectroscopy, X-Ray Crystallography, and Theoretical Calculations, Pharmaceutical Society of Japan, Aug. 2003, Chem. Pharm. Bull 51(18), pp. 929-934.
International Search Report, PCT/EP2014/063704, date of mailing Jul. 17, 2014, 3 pages.
European Search Report, 13173979.9, date of mailing Dec. 18, 2013, 10 pages.

* cited by examiner

PREPARATION OF GRIGNARD REAGENTS USING A FLUIDIZED BED

RELATED APPLICATIONS

This application is a U.S. National Stage of International Application No. PCT/EP2014/063704, filed on Jun. 27, 2014, which claims priority to European Patent Application No. 13173979.9, filed Jun. 27, 2013, the entire contents of which are incorporated herein by reference.

The present invention relates to a process of preparing a Grignard reagent comprising creating a fluid of magnesium particulates such as for example, in a fluid bed reactor. In one embodiment, the magnesium particulates are suspended, for example within a reactor, with a solvent that is a liquid or a gas flowing at a velocity sufficient such that the particulates behave as a fluid. The present invention further relates to a process comprising fluidizing the magnesium particulates to form a Grignard reagent, and reacting the Grignard reagent with a substrate as part of a synthetic process.

Although Grignard reagents are the most commonly used alkylating agents for the preparation of metal alkyls, aryls, and alkenyls, the methods by which they are made and used have hardly changed since the time of Grignard himself. Their batch wise synthesis may require ingenuity to get the reaction initiated, especially with chlorides. After an induction time, the Grignard reaction seems to go autocatalytically, meaning that once a critical amount of the Grignard reagent has formed, new active centers are exposed and subsequently the rate of reaction increases exponentially. The runaway reaction is only stopped when one reactant is consumed. Since Grignard reactions are highly exothermic, a thermal explosion could occur if a large amount of organic halides was added during a long induction time. Yields are also often disappointingly low, particularly where coupling reactions may occur, and the scale in the laboratory is limited to a few liters of molar solution. For example, in the pharmaceutical industry, Grignard reagents are of enormous importance as an initial stage of numerous multi-step organic syntheses. An analysis of the top 50 drugs suggests that around 10% of all synthesis routes contain one or more Grignard steps.

The prior art is characterized by processes for preparing Grignard reagents that are discontinuous or batch-wise, using magnesium turnings. These processes are not optimized for large industrial scale production of Grignard reagents, despite the industry's continued reliance on them to set-up carbon-carbon bonds in compounds, for example, active pharmaceutical ingredients. Grignard reagents are conventionally prepared by reacting an organohalide with magnesium metal in an organic solvent. Since the reaction is problematic to initiate and maintain, but also can proceed explosively if not carefully controlled, cumbersome reaction conditions and safety precautions are necessary with industrial scale reactions. For example, the standard approach using magnesium turnings in a batch reactor has several disadvantages (poor heat and mass transfer can lead to a runaway, difficult to initiate the reaction, and potential batch-to-batch variation). Specifically, an oxide layer which forms on the surface of magnesium turnings, slows the Grignard reaction and prevents further reaction with an organohalide. Activation of magnesium in a batch process has the disadvantage of adding another reagent to the mix, is often a slow process, leads to consumption of magnesium, and may induce uncontrollable reaction rates after a threshold level of Grignard reagent is formed. Batch Grignard preparations have high exothermicity and the resulting elevated temperatures lead to preparatory scales of production that are less than desirable. Often such preparations have to be restarted with fresh reagents and require another round of magnesium activation.

Continuous processes for performing the Grignard reaction have been described in literature as well. DE1293767 discloses a process wherein Mg particles are contacted with at least one organohalide by feeding organohalide dissolved in cyclic ether to the bottom of a column that is filled with—and replenished from the top with—Mg turnings. In U.S. Pat. No. 2,464,685 a continuous process for effecting reaction between Mg and organohalide is described, wherein the organohalide in ether solution is supplied to a body of Mg particles under continuous agitation. U.S. Pat. No. 4,105,703 describes a continuous Grignard process wherein cyclohexyl halide solution is fed to the bottom of a column-like reactor packed with magnesium shavings, which are fed from the top of the column. In U.S. Pat. No. 3,911,037 Grignard reagent is made continuously by feeding organohalide and solvent to at least one stirred reaction vessel, while concurrently feeding Mg and withdrawing product overflow. Drawbacks of such processes using e.g. stirred bed or packed column reactors include non-optimal heat and mass transfer during highly exothermic reaction.

SUMMARY OF THE INVENTION

The present invention provides a process of preparing a Grignard reagent comprising creating a fluid of magnesium particulates and a solvent in a reactor; and contacting the magnesium particulates with at least one organohalide to form the Grignard reagent, wherein the fluid comprises the solvent flowing against gravity through a bed of magnesium particulates that range in size from 10 to 1000 µm when added, with a flow rate ranging from 0.1 to 0.3 cm/s in at least part of the process to create a fluidized bed of magnesium particulates in the solvent.

A continuous process that fluidizes the magnesium particulates when forming the Grignard reagent and during reaction with a substrate provides a more productive, safer and more flexible process compared to a batch process or even to a continuous process having a packed bed.

In a preferred way of operating, the process of the invention is a continuous process that comprises creating a fluid of magnesium particulates and a solvent in a reactor column; contacting the magnesium particulates with at least one organohalide to form the Grignard reagent, and contacting the Grignard reagent with a substrate.

In one embodiment, the present invention provides a continuous process of preparing a Grignard reagent, comprising reacting magnesium particulates in a fluid-bed reactor, and forming the Grignard reagent continuously for reaction with a substrate, and wherein a feeder of fresh magnesium continuously replenishes any magnesium consumed during the preparatory process.

In another embodiment, the present invention provides a process of maintaining a uniform temperature gradient during preparation of a Grignard reagent, comprising reacting magnesium particulates with an organohalide solution in a fluid bed reactor.

DETAILED DESCRIPTION OF THE INVENTION

Figure 1:
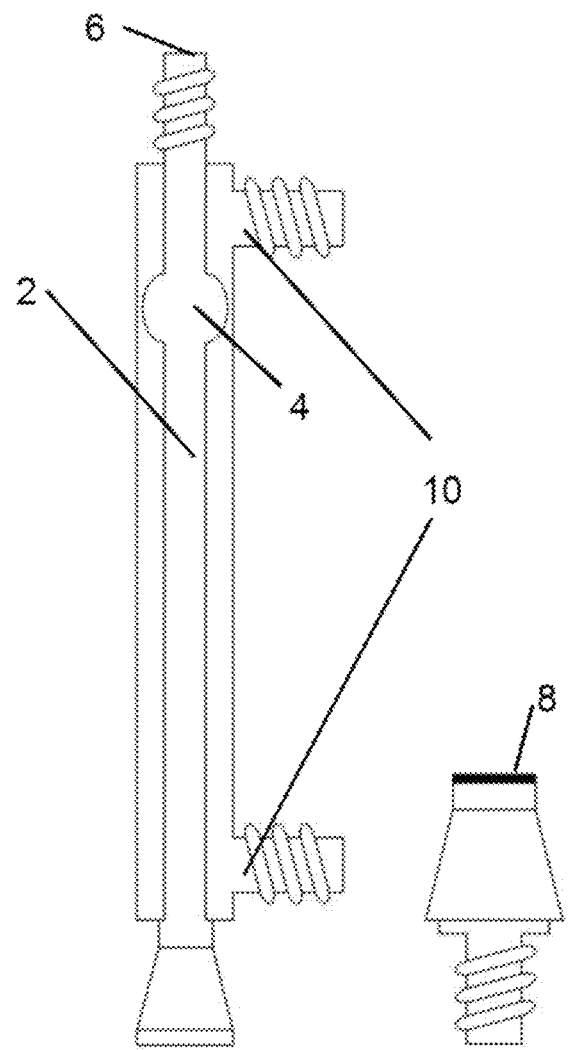
FIG. 1 depicts a single bulb glass reactor

As used herein, a fluid results from a mixture of solid particles and a solvent when the flow rate of the solvent is higher than the settling velocity of the solid particles. For example, the term "fluid bed" or "fluidized bed" means a bed of particles through which solvent flows against gravity with a flow rate sufficient so that the bed is loosened and the particle-solvent mixture behaves as though it is a fluid. In one embodiment, an entire bed of magnesium particulates behaves as though it is a fluid. In another embodiment, an entire bed of magnesium particulates behaves as though it is a fluid when the flow rate of an organohalide solution is higher than the settling velocity of the magnesium particulates in at least a part of the process. The term 'in at least part of the process' within the context of this application is understood to mean that a fluid is formed of the combination of particulates of indicated size and solvent flowing at indicated flow rate at or during at least a certain phase, place or time while performing the process, but not necessarily at any such phase, place or time while performing the process, because continuing reactions and replenishment of reactants may result in different combinations as well. Especially size of Mg particles will vary in time during the process, as the particles are consumed during the reaction and optimum flow rate, which depends on particle size, may thus also vary.

"Organohalides" are compounds known in the literature. As used herein, organohalides include any organic halides that are applicable to the manufacture of Grignard reagents. In one embodiment, the organohalide is chosen from an alkyl halide, aryl halide, and arylalkyl halide, wherein each of alkyl, aryl and arylalkyl is optionally substituted with substituents independently chosen from straight or branched alkyl, monocyclic or bicyclic rings, alkylmonocyclic or alkylbicyclic rings; partially saturated or aromatic; carbocyclic or heterocyclic, and which carbocyclic or heterocyclic rings are optionally substituted. In yet another embodiment, the organohalide is a synthon utilized in the manufacture of an active pharmaceutical ingredient. In another embodiment, organohalides are those compounds with boiling points below about 300° C. chosen with intent to analyze on gas chromatography. In one embodiment, the halide in organohalide is chosen from Cl, Br, and I. In another embodiment, organohalides are those compounds with boiling points above about 300° C. chosen with intent to analyze by other means than gas chromatography.

The present invention provides a process of preparing a Grignard reagent comprising creating a fluid of magnesium particulates and a solvent, such as in a preferred embodiment in a fluid bed reactor, and contacting the magnesium particulates with an organohalide. In a preferred embodiment, the solvent comprises the organohalide in a liquid or gas form. The solvent may also comprise other liquids or gases in addition to the organohalide. In one embodiment, a solvent is used to fluidize the magnesium particulates and the fluid is later brought into contact with the organohalide to form the Grignard reagent. In another embodiment, the solvent is a gas comprising an organohalide in a gas form. In this embodiment, methylchloride is the preferred solvent.

In one embodiment, the present invention provides for a fluidized bed of magnesium particulates.

In another embodiment, the bed of magnesium particulates is loosened and suspended when the solvent, for example, a high velocity gas or liquid, passes through it, so that the entire bed behaves as though it were a fluid.

The magnesium particulates can be of any size which facilitate uniform particle mixing and/or maintain a uniform temperature gradient within, for example, a fluidized bed. In one embodiment, the particulates range in size from about 10 μm to about 1000 μm; or from about 100 μm to about 500 μm. In another embodiment, the particulates range in size from about 200 μm to about 400 μm. Here, particulate size refers to the largest dimension of the particle when introduced to the fluidized bed. For a spherical particle, the size is hence the diameter of the particle. In yet another embodiment, the present invention relates to minimizing hot spot formation, a problem frequently encountered in packed beds or when using magnesium turnings, and which has been overcome by the use of fluidized magnesium particles.

In yet another embodiment, the magnesium particulates behave as a fluid when the flow rate of the solvent, such as an organohalide or an organohalide with another liquid or gas is higher than the settling velocity of the magnesium particulates. Table 1 below shows the settling velocity of various diameters of spherical magnesium particles in liquid solvents.

TABLE 1

Settling velocities of spherical magnesium particles with different diameters.

| Particle Diameter μm | Density solvent g/cm³ | Settling velocity cm/s |
|---|---|---|
| Solvent: THF | | |
| 100 | 0.89 | 0.01 |
| 200 | 0.89 | 0.038 |
| 250 | 0.89 | 0.059 |
| 400 | 0.89 | 0.15 |
| 1000 | 0.89 | 0.95 |
| Solvent: CPME | | |
| 100 | 0.785 | 0.01 |
| 200 | 0.785 | 0.043 |
| 250 | 0.785 | 0.067 |
| 400 | 0.785 | 0.17 |
| 1000 | 0.785 | 1.00 |

In another embodiment, the magnesium particulates have a size in the range of 200-250 μm, with a settling velocity in the range of about 0.03 to 0.07 cm/s. Accordingly, the flow rate of the organohalide is adjusted to be higher than the settling velocity of magnesium particulates. In one embodiment, the flow rate of the organohalide is in the range of about 5 to about 10 mL/min. In another embodiment, the flow rate of the organohalide is in the range of about 0.1 cm/s to about 0.3 cm/s in a part of the process where magnesium particulates create a fluidized bed. In yet another embodiment, the flow rate of the organohalide is in the range of about 0.1 cm/s to about 0.2 cm/s in a part of the process where magnesium particulates create the fluidized bed to completely suspend all of the magnesium particles.

A fluidized magnesium allows for excellent contact of particulates with any fluid (gas or liquid), which means higher reaction efficiency and quality. In one embodiment, the fluidized bed relates to a high bed-to-surface heat transfer coefficient. In yet another embodiment, nearly uniform temperatures are maintained under highly exothermic reaction conditions, which is very difficult or not feasible when using a conventional packed bed.

A further advantage of present process is that no hot spots are formed in the reactor and a uniform temperature distribution is maintained during preparation of the Grignard reagent. Without wishing to be bound to any theory, the inventors think this relates to a fluidized magnesium bed providing better access to the surface of the magnesium particles, better heat transfer between magnesium and solvent, and more predictable change in surface area over time.

In a preferred embodiment, the fluidized bed of magnesium is contained in a reactor column. The reactor column may for example be of glass, metal (such as for example steel or stainless steel), or contain polymeric material (such as Teflon). Preferably, the reactor column is a glass or a metal column.

For example, in a preferred embodiment, a glass reactor column according to the present invention comprises a vertical tube, 2, with an expansion bulb, 4, at the top of the reactor to reduce flow rate so as to prevent the magnesium particles from overflowing at the exit, 6, since the flow rate against gravity of the solvent is lower than the settling velocity of the magnesium particulates in the expansion bulb. This is schematically illustrated in FIG. 1. In one embodiment, the length of the vertical column is about 41 cm and diameter is about 0.9 cm. In yet another embodiment, the glass column is equipped with a filter, 8, such as a 10 µm filter, near the bottom of the glass column, 2, to prevent the magnesium particulates from entering the pump. In one embodiment, the glass reactor is used at temperatures below the boiling point of the solvent by controlling the temperature via heat exchanger 10.

In another preferred embodiment, a metal tube reactor according to the present invention has the advantage of pressurizing the reactor to reach a higher reaction temperature, and/or prevent boiling of the solvent when working at temperatures above the boiling point at 1 bar. In one embodiment, the reactor placed at high temperatures ensures the reaction is finished within a short time. In another embodiment, the residence time of the organohalide in the reactor is minimal and ranges from about 0.1 minutes to about 10 minutes, or from about 1 minute to about 3 minutes.

Figure 2:
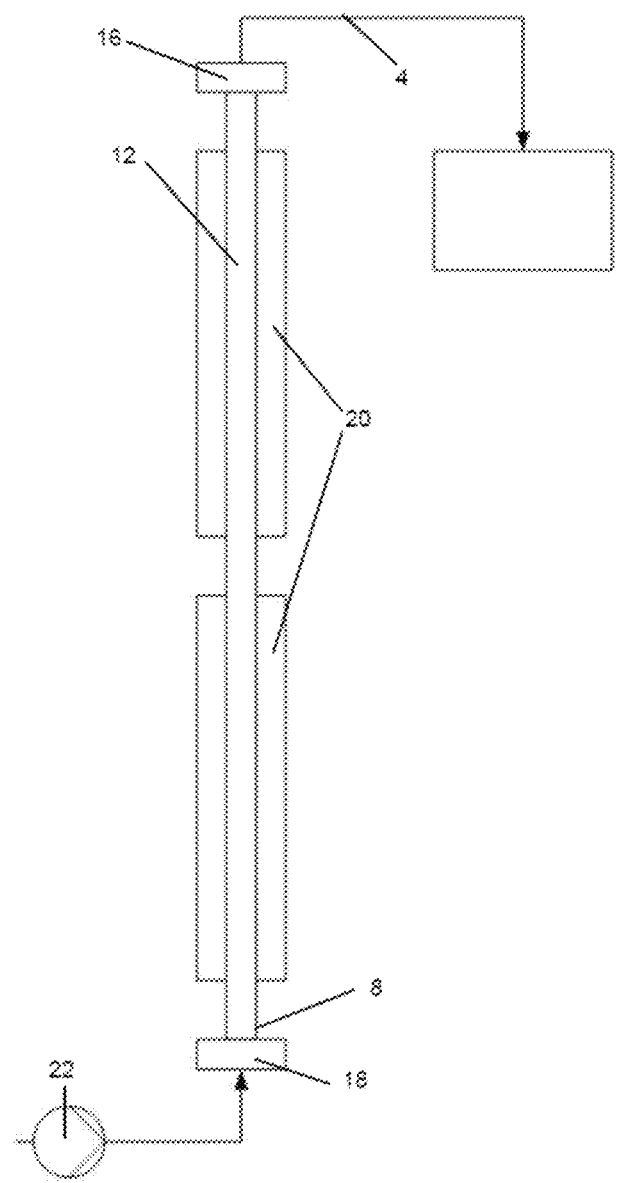
FIG. 2 depicts a double-walled stainless steel reactor

In a preferred embodiment, pressurization constricts the magnesium particulates and prevents them from exiting the column. FIG. 2 illustrates a schematical representation of a metal reactor. In one embodiment, the reactor comprises a double-walled column, 20, for heating or cooling the reaction mixture, 12. In another embodiment, the reactor may further comprise a stainless steel expansion bulb to decrease flow rate when magnesium particles are consumed. In yet another embodiment, the reactor may further comprise pressure valves at the top, 16, and bottom, 18, of the reactor. The top pressure valve prevents an overflow of magnesium particles from exiting the system and the bottom pressure valve functions as a damper for the pump, 22. In yet another embodiment, the pressure difference between the top and bottom pressure valves is approximately 0 bar. After the reactor the product is transferred, 4, to a further reactor, such as a micro reactor, or collected in a container.

The temperature may be regulated by an external thermostat and validated by an internal thermocouple in the reactor. In one embodiment, the reactor is maintained at temperatures in the range of about 50° C. to about 150° C., or from about 75° C. to about 125° C. For slow Grignard reactions, the reaction rate is increased by increasing the temperature of the reactor under pressure. In another embodiment, a slow Grignard reaction involves use of an organochloride.

The preferred residence time of the magnesium particulates with the organohalide will depend on the organohalide, other solvents present if any, and the temperature. For example, at a higher temperature a lower residence time may be necessary to activate the Grignard reaction. One of skill in the art will know to vary the flow conditions, temperature and residence time based on the specific reactants in order to optimize reaction conditions.

Different lengths of the reactor column can be used to vary the residence time of the organohalide within the column. In one embodiment, the length of the column is in the range of about 25 cm to about 150 cm, or from about 40 cm to about 110 cm. In yet another embodiment, the length of the column is chosen from 49.5 cm, 75 cm, and 106 cm. In one embodiment, a reactor with smaller dimensions gave better heat and mass transfer, and thus was better able to handle the highly exothermic Grignard reagent formation. In another embodiment, the volume of the column is in the range of about 25 $cm^3$ to about 150 $cm^3$, or from about 40 $cm^3$ to about 110 $cm^3$. In yet another embodiment, the metal column is equipped with a 10 µm filter near the bottom of the column to prevent the magnesium particulates from entering the pump. In another embodiment the metal is stainless steel.

In one embodiment a reactor column has a diameter chosen for its suitability in the targeted Grignard preparation. In yet another embodiment, the inner diameter of the column is in the range from about 0.4 cm to about 3 cm, or from about 0.7 cm to about 1.5 cm. In yet another embodiment, the inner diameter of the column is about 1.1 cm.

In another embodiment, the inner diameter of the expansion bulb i.e. a section of the reactor or a section arranged on after the reactor that prevents overflow (if present) can be of any diameter suitable for the intended Grignard preparation. In yet another embodiment, the inner diameter of the bulb is from about 2 to 7 times the inner diameter of the reactor column.

In a preferred way of operating, the present invention provides a continuous process comprising fluidizing magnesium particulates in a reactor, forming the Grignard reagent continuously, and reacting the Grignard reagent with a substrate.

Grignard reagents are highly air and moisture sensitive and therefore difficult to store. In one embodiment of the present invention, the Grignard reagent once formed is consumed in-situ in a subsequent reactor, for example a microreactor, in presence of a substrate to obtain the desired product.

In another embodiment, the column filled with magnesium particulates is replaced when the magnesium is consumed. In yet another embodiment, a replacement cartridge with magnesium particulates may replace an initial cartridge with magnesium particulates to replenishes magnesium consumed in reaction with substrate. In yet another embodiment, an array of replaceable cartridges with magnesium are placed in parallel so that magnesium can be replenished by replacing one or more cartridges of the array without interrupting or stopping the reaction with substrate.

In a preferred embodiment, the Grignard reagents are produced in low-boiling ethereal solvents chosen from tetrahydrofuran, methyltetrahydrofuran, dioxane, dimethoxyethane and cyclopentyl methyl ether or a mixture thereof. In another embodiment, the Grignard reagent is produced in cyclopentyl methyl ether (CPME). The use of low boiling solvents creates an overpressure that keeps air out of the system, while the use of CPME allows for higher reaction temperatures resulting in faster reaction times. Also, as Grignard reagents are moisture-sensitive, CPME has the advantage of lower water solubility over the other ethereal solvents. In one embodiment, the use of CPME increases shelf life of the prepared Grignard reagent and also allows for recycling of the solvent by phase separation and distillation.

In another embodiment of the present invention, the magnesium particulates used have a natural oxide layer formed on its surface. Activation of magnesium particulates is then undertaken by removing the oxide layer with 1,2-dibromoethane, iodine etching, or pre-flushing the particulates with existing Grignard reagent. In one embodiment, the activation uses a pre-flush with existing Grignard reagent. In another embodiment, the reactor with magnesium particulates is heated in presence of an existing Grignard reagent.

In yet another embodiment, the magnesium particulates in a fluid bed of the present invention have a size in the range of 200-250 μm, with a settling velocity in the range of about 0.03 to 0.06 cm/s. Accordingly, the flow rate of the organohalide through small particulates will force the magnesium to overflow from the top of the reactor.

Figure 3:
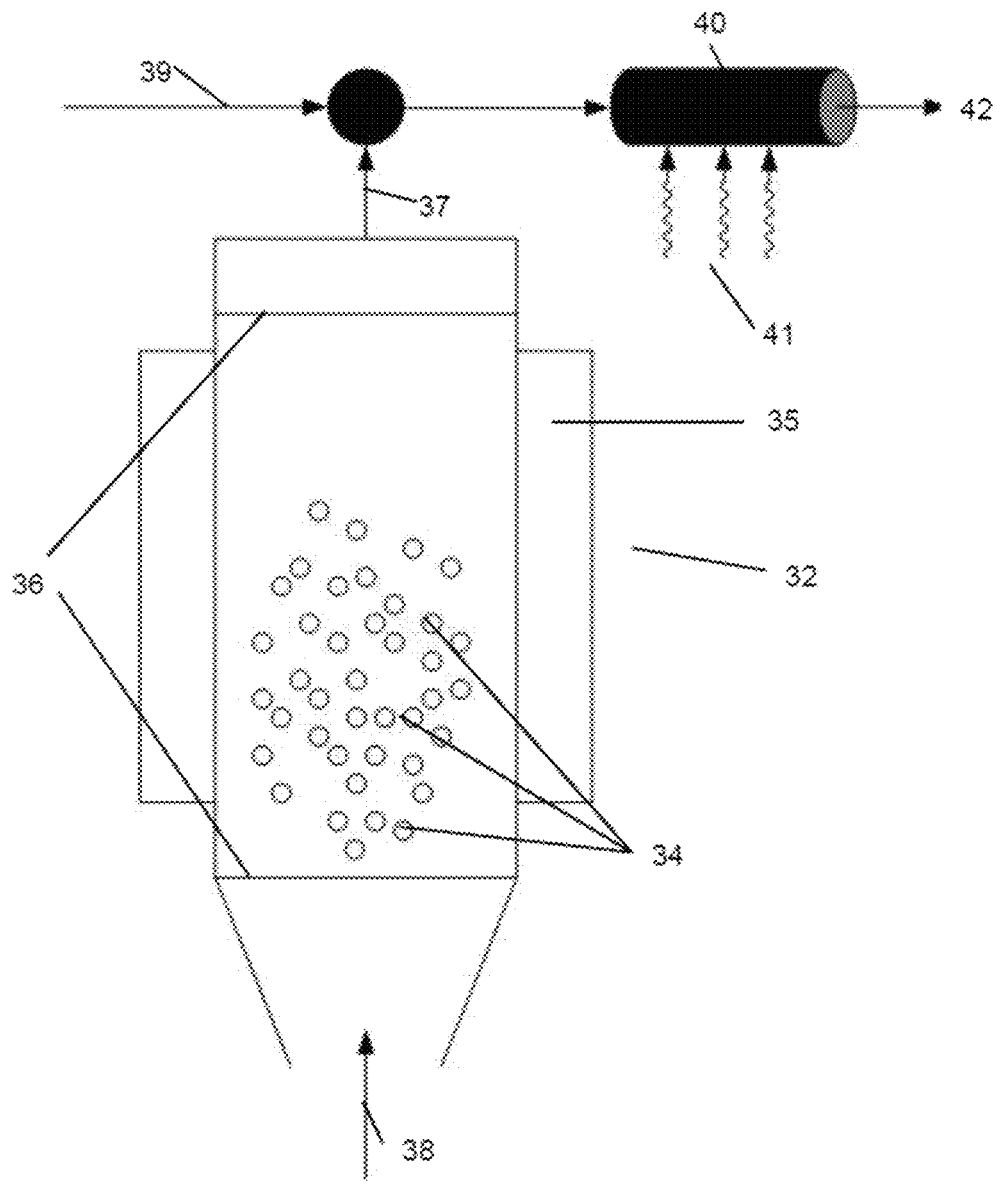
FIG. 3 depicts a schematic for an in-situ continuous Grignard reaction set-up

In another embodiment, the Grignard reagent formed is consumed subsequently in a further reactor without stopping and (re)starting the reaction by mixing or contacting the Grignard reagent with the substrate to make the desired product. FIG. 3 depicts a fluidized bed reactor, 32, half filled with 200-400 μm magnesium particulates, 34, supported by a frit, 36, at both ends. The magnesium particles, 34, are suspended by pumping the organohalide solution, 38, against gravity and flowing at a higher velocity than the settling velocity of magnesium particulates. The reactor, 32, is kept at a temperature of about 100° C. by a heat exchanger, 35, ensuring a short residence time. The Grignard reagent, 37, thus formed is consumed continuously by mixing with the substrate, 39, in a microreactor, 40, which microreactor may be heated or cooled, 41, to yield the desired product, 42.

The processes of the present invention achieve a high yield of formation of the Grignard reagent. In one embodiment, the yields of the Grignard reagent vary from about 70% to near quantitative yield. In another embodiment, a high yield of conversion is obtained for any organohalide that forms Grignard reagents poorly in a batch process. Additional compounds were also tested in the continuous process. Table 2 gives an overview of some of the compounds tested and their percent conversion to product.

TABLE 2

Overview of compounds utilized in a continuous fluid bed Grignard preparation

| Exp. | Organohalide | Reactor* | Solvent | Temp (° C.) | Flow (ml/min) | RT# (min) | Conversion (%) |
|---|---|---|---|---|---|---|---|
| 1 | iodobenzene | Glass | CPME | 95 | 5 | 7 | 84 |
| 2 | iodobenzene | 1 | CPME | 95 | 5 | 10 | 0 |
| 3 | iodobenzene | Glass | CPME | 95 | 5 | 7 | 79 |
| 4 | Bromobenzene | Glass | CPME | 95 | 5 | 7 | 93 |
| 5 | iodobenzene | 1 | CPME | 95 | 5 | 10 | 92 |
| 6 | Cyclopropyl-bromide | 1 | CPME | 25 | 5 | 10 | 70 |
| 7 | methyl chloride | 1 | MTBE/CPME | 80 | 5 | 10 | — |
| 8 | methyl chloride | 1 | THF/CPME | 60 | 5 | 10 | — |
| 9 | methyl chloride | 1 | CPME | 100 | 5 | 10 | 94 |
| 10 | methyl chloride | 1 | THF | 100 | 5 | 10 | 98 |
| 11 | methyl chloride | 1 | THF | 100 | 5 | 10 | 98 |
| 12 | methyl chloride | 1 | THF | 80 | 5 | 10 | — |
| 22 | bromo tert butylbenzene | 3 | THF | 110 | 5 | 10 | 45 |
| 23 | bromo tert butylbenzene | 3 | THF | 110 | 5 | 10 | 87 |
| 24 | bromo benzaldehyde dimethyl acetal | 2 | THF | 80 | 5 | 15 | 90 |
| 25 | bromo benzaldehyde dimethyl acetal | 2 | THF | 100 | 5 | 15 | 95 |

*1, 2 and 3 are all steel reactors of same design but the reactor was changed as wear of the reactor was progressing.
RT = Residence time halide is adjusted to be higher than the settling velocity of magnesium particulates. In one embodiment, the flow rate of the organohalide is in the range of about 5 to about 10 mL/min. In another embodiment, the flow rate of the organohalide is in the range of about 0.1 cm/s to about 0.3 cm/s. In yet another embodiment, the flow rate of the organohalide is in the range of about 0.1 cm/s to about 0.2 cm/s to completely suspend all of the magnesium particles. A small particle size is in general not considered desirable in Grignard reactions by one of skill in the art, as its use would lead to faster heat build-up, or alternatively, a higher flow The present invention may also provide a fully continuous process of preparing a Grignard reagent comprising, reacting fluidized magnesium particulates in, for example a fluid-bed reactor, and forming the Grignard reagent continuously for reaction with a substrate. In a preferred embodiment, a feeder of fresh magnesium continuously replenishes any magnesium consumed. In a particularly preferred embodiment, a grinder device is attached to a cutting chamber, which in turn may be attached to a continuous Grignard reactor. In another embodiment, the purpose of including a grinder step is to make the Grignard process safer as smaller amounts of magnesium will be available at any time, minimizing the exposure of magnesium to both solvent and air.

In one embodiment, the Grignard reagent flows into contact with the substrate, which is stationary. In an alternative embodiment, both the Grignard reagent and the substrate are flowing.

The present invention also provides for downstream industrial scale processes that rely on a fluidized bed process of preparing a Grignard reagent. In one embodiment, Grignard reagents from pharmaceutical starting materials are prepared continuously for reaction with a substrate In one embodiment, the high conversion rate of the Grignard reaction makes the downstream synthetic processes viable to be performed on an industrial scale.

The processes of the present invention have advantages because first, the Grignard reaction does not have to be started or stopped intermittently but can be operated continuously and second, the Grignard reagents are formed in high yield. This translates into a faster scale-up and commercialization but also benefits production scale from the higher yields of the Grignard reagent reaction with substrates.

In another embodiment, a Grignard reagent of bromo-t-butylbenzene is used in the manufacture of active drug product, LSN2401292. Scheme 1 below depicts the use of the Grignard reagent tert-butyl(phenyl)magnesium bromide in the manufacture of an active drug product, LSN2401292.

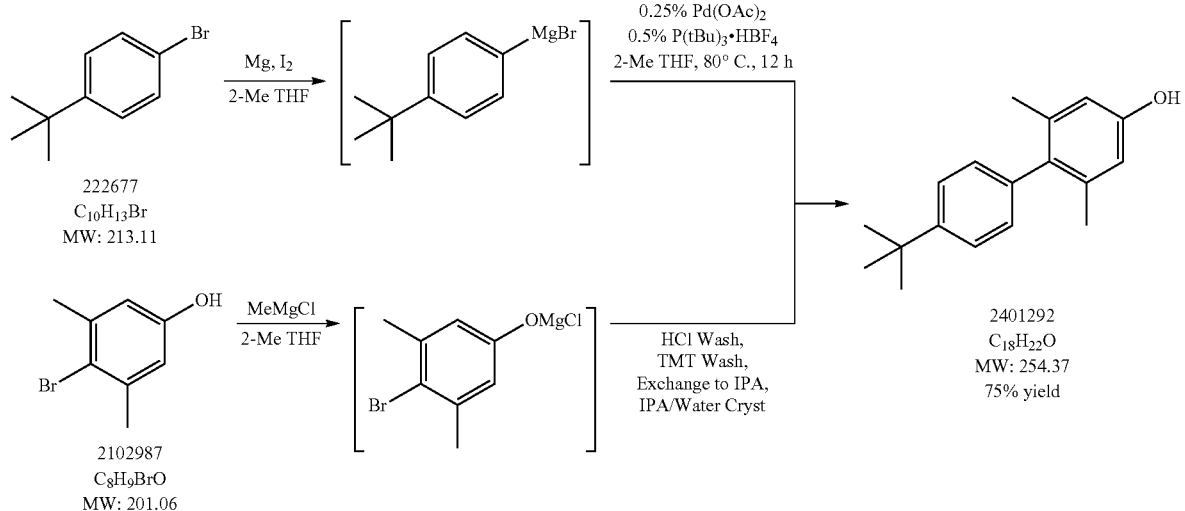

Scheme 1

In a further embodiment, valsartan, which is an angiotensin II receptor antagonist (more commonly called an "ARB", or angiotensin receptor blocker), with particularly high affinity for the type I (AT1) angiotensin receptor, is produced following Scheme 2.

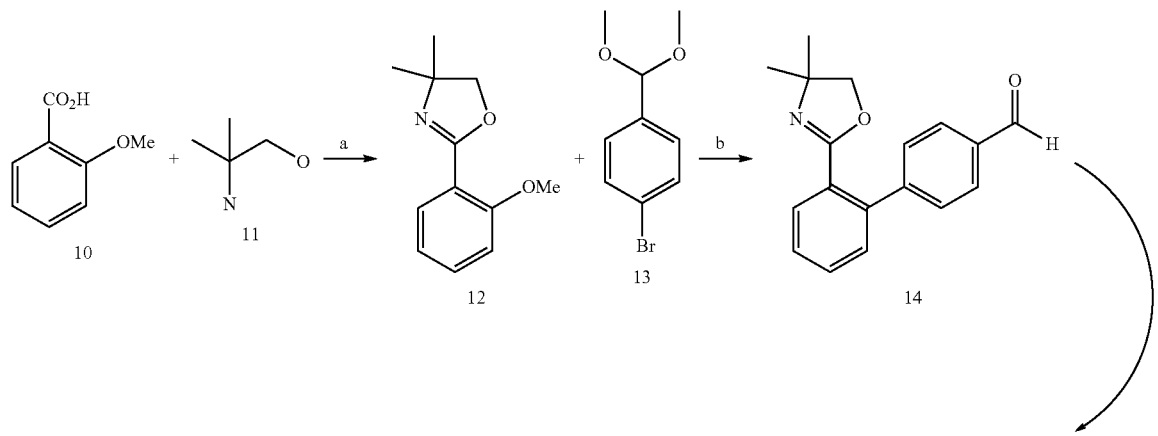

Scheme 2.

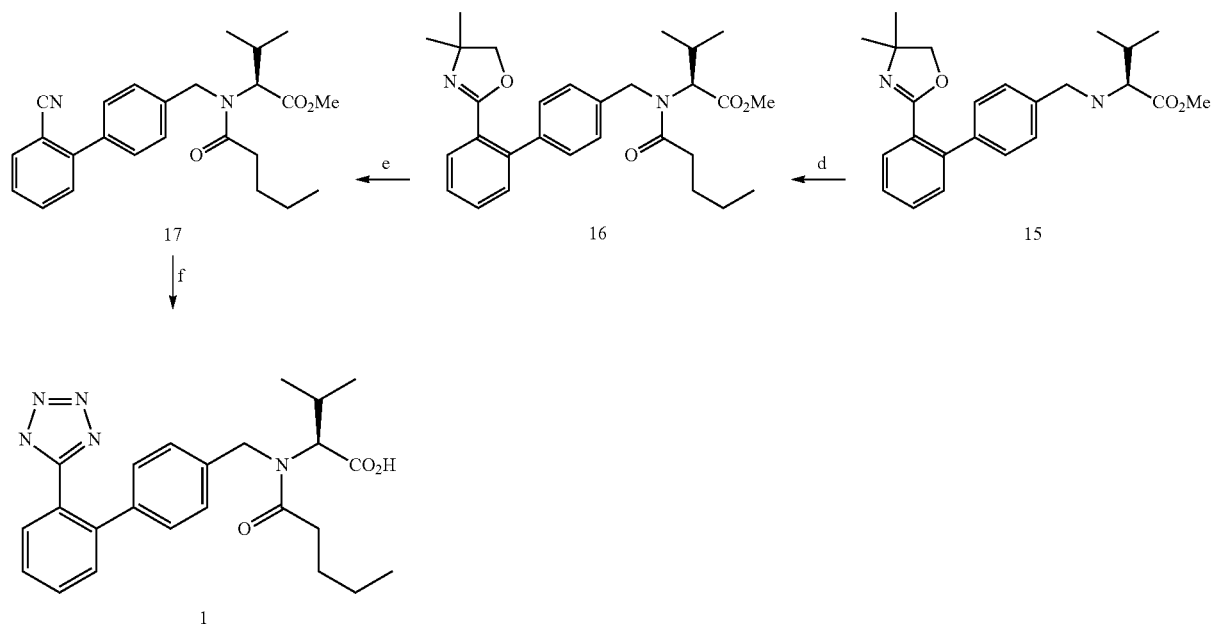

Scheme 2 above shows the synthesis of valsartan using inexpensive and commercially available O-anisic acid. One of the intermediate steps involves formation of Grignard reagent of bromo-4-(dimethoxymethyl) benzene via fluidized magnesium particulates which may be further reacted with the oxazoline compound (12) in a continuous process using a fluid bed.

Figure 5:
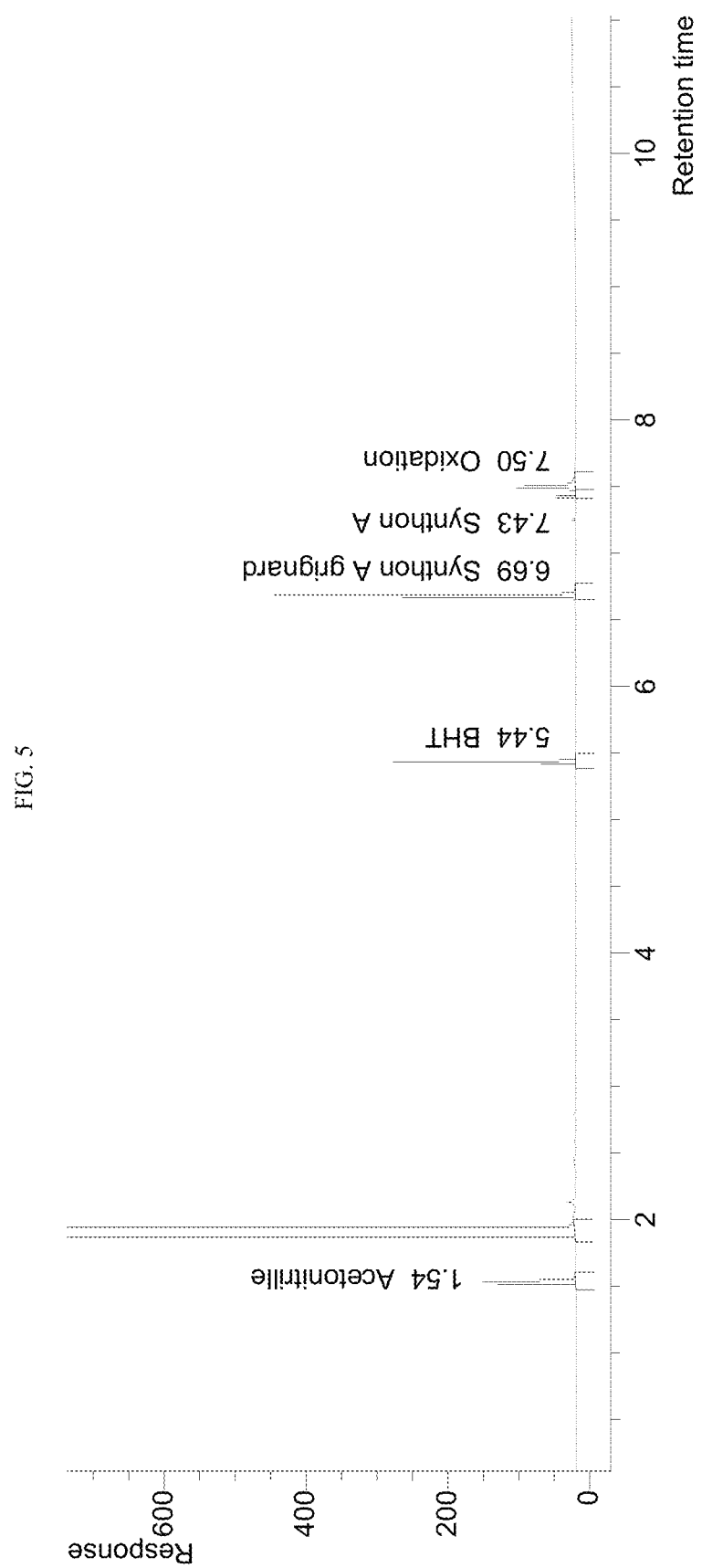
FIG. 5 is a gas chromatogram depicting over 90% conversion of synthon A to synthon A Grignard reagent. The conversion represents a key first step in the synthesis of the active drug product, aliskiren.

In one embodiment, Grignard reagents from pharmaceutical starting materials (synthon A) are prepared continuously for reaction with a substrate (synthon B). Schemes 3a-b below depict the use of a Grignard reagent in the manufacture of an active drug product, aliskiren. FIG. 5 is a gas chromatogram depicting the over 90% conversion of synthon A to synthon A Grignard reagent.

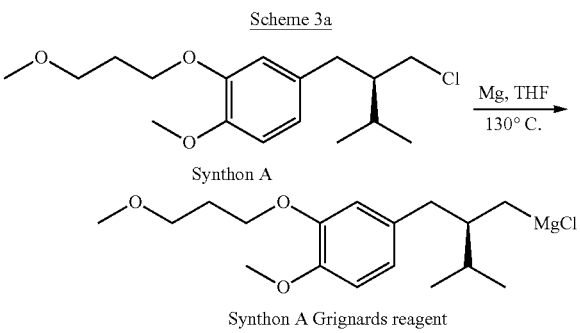

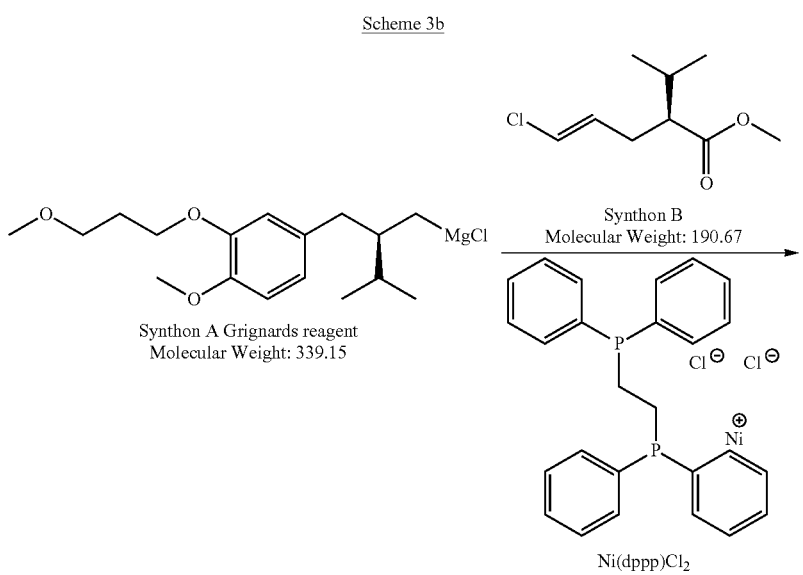

-continued

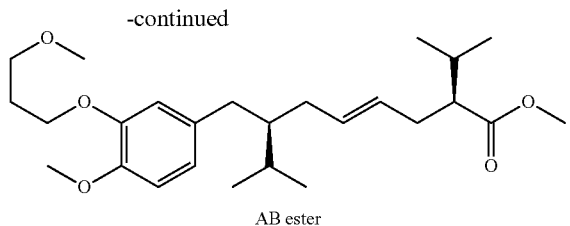

AB ester

EXAMPLES

The present invention will now be described in greater detail by the following non-limiting examples. It is understood that the skilled artisan will envision additional embodiments consistent with the disclosure provided herein.

The use of any and all examples, or exemplary language (e.g., "such as") provided herein, is intended merely to better illustrate the invention and does not pose a limitation on the scope of the invention unless otherwise claimed. No language in the specification should be construed as indicating any non-claimed element as essential to the practice of the invention. Several embodiments of this invention are described herein, including the best mode known to the inventors for carrying out the invention. Variations of those embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements and embodiments, i.e. preferred ways of operating the process of the invention, in all possible variations thereof is considered to be disclosed herein and encompassed by the invention unless otherwise indicated herein, or unless otherwise clearly contradicted by the context or recognized as clearly (physically) not feasible by a skilled person.

Gas chromatography (GC) analyses were performed as described below:
Instrument used: Agilent technologies gas chromatograph (7890A series) fitted with an Agilent technologies (7693 series) auto sampler.
Flushing agent: acetonitrile
Gradient: 2 min at 50° C.; 20° C./min to 280° C.; followed by 5 min at 280° C.
0.5% (V/V) of samples in CPME or THF were analyzed (10 µl sample in 2 ml solvent using a micro pipette) by injecting directly on the GC.

Example 1

Production of a Grignard Reagent in a Fluid Bed with Iodine Activation

Parameters:
Column composition: Glass
Length of column: 41 cm
Inner diameter of column: 0.9 cm
Volume of column: 29 mL
Extra volume (connectors): 3 mL
Pore size frit: 10 µm
Pump: Gilson HPLC pump 50 mL pump head
Tubing from pump: Swagelok 1/16" SS tubing 1 mm ID
Tubing from reactor: Teflon 1/8" tubing 2.4 mm ID Iodine crystals and 10.3 g (0.42 mol) 250 µm Mg particles were introduced in a reactor and the reactor was filled with dry CPME until all particles were immersed, and left at RT for 10 minutes. Thereafter, the reactor was flushed with CPME to result in a clear solution. After activation of the reaction, 1M solution of PhI in CPME was added at 5 ml/min, the reactor heated to 95° C. (internal temperature of 85° C.) and left for 10 min. At this point, bubbles were seen at the exit tubing of the reactor. 1M PhI solution was pumped through at 5 ml/min, with the solution turning brownish. The product collected in dry round bottom flasks under nitrogen. No magnesium particles were observed exiting the reactor. 5 ml of product was loaded in a dry inert flask and stirred at RT (theoretically containing 5 mmol at 100% conversion). 0.51 ml (5 mmol) of benzaldehyde was added via a syringe. The solution coloured bright yellow, with temperature and viscosity increasing. Then, the reaction mixture was diluted with dry CPME, and after 10 min. stirring washed twice with 10% sulfuric acid resulting in a yellow CPME layer and clear water layer. A reddish oil that solidified at ambient temperature was isolated from the ether layer. Titration with menthol and 1,10-phenatroline gave a red color, indicating the RMgX product had formed at 55-75% conversion. GC-MS analysis revealed a peak of diphenylmethanol (Mw 154) in the GC chromatogram.

Example 2

Continuous In-Situ Grignard Reaction with Benzaldehyde

Parameters:
Column composition: Stainless steel
Length of column: 49.5 cm
Inner diameter of column: 1.1 cm
No bulb with larger diameter near top
Volume of column: 47 mL
Extra volume (connectors): 3 mL
Pore size frit: 10 µm SS
Pump: Gilson HPLC pump 50 mL pump head
Tubing from pump: Swagelok 1/16" SS tubing 1 mm ID
Tubing from reactor: Teflon 1/8" tubing 2.4 mm ID.

10.0 g (0.41 mol) of 250 µm Mg particles were introduced in a reactor and the reactor filled with 0.9 M Grignard solution in CPME, heated to 95° C. and left for 10 minutes. After activation of the reaction, 1M PhI in CPME was flushed through the column at 5 mL/min and the first 50 mL were collected in a schlenck tube for future use. The Grignard reagent and the aldehyde (10% benzaldehyde) were introduced by a 1/8" SS Swagelok t-piece to ensure that the jets were perpendicular to each other to prevent solid formation in the t-piece.

The product, a suspension of CPME and the magnesium salt of the product were collected in a stirred round bottom flask containing 10% $H_2SO_4$ to directly hydrolyze the salt to the desired alcohol.

It was observed that the Grignard reaction yielded a slurry which resulted in build-up of resistance in the column. To solve this problem, the propelling forces of the RMgX solution and the aldehyde solution were each adjusted so that the two solutions did not mix in the entry lines. The RMgX as well as the aldehyde were both pumped at 5 ml/min using a ~10% solution in CPME. The theoretical residence time was calculated to be 1.51 min. 3 samples were collected in 10% $H_2SO_4$, the phases separated and analyzed on GC. All samples showed a greater than 90% conversion.

Example 3

Production of a Grignard Reagent in a Glass Reactor with PhMgI as Activator

Figure 4:
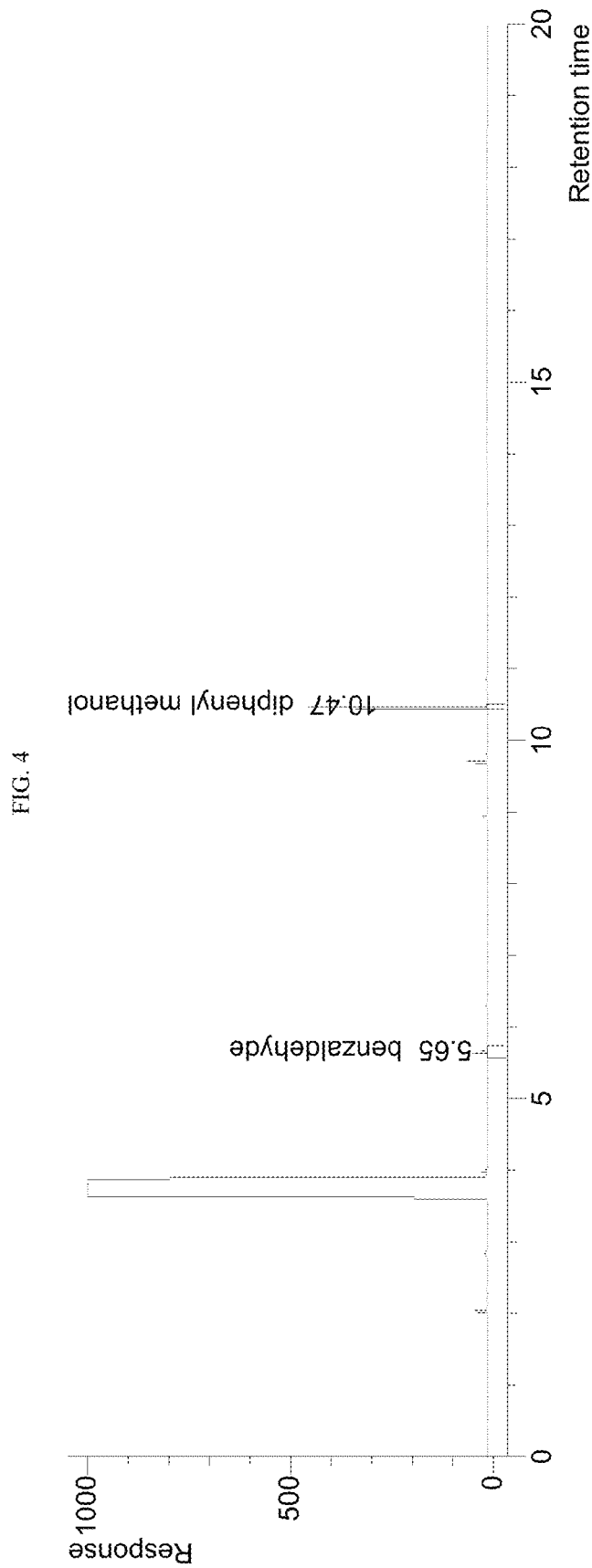
FIG. 4 is a gas chromatogram depicting over 90% conversion of phenylbromide to diphenyl methanol using phenyl magnesium bromide as the Grignard reagent

Parameters:
Column composition: Glass triple bulb
Length of column: 41 cm
Inner diameter of column: 0.9 cm
No bulb with larger diameter near top
Volume of column: 29 mL
Extra volume (connectors): 3 mL
Pore size frit: 10 μm
Pump: Gilson HPLC pump 50 mL pump head
Tubing from pump: Swagelok 1/16" SS tubing 1 mm ID
Tubing from reactor: Teflon 1/8" tubing 2.4 mm ID 10.1 g (0.42 mol) of 250 μm Mg particles were introduced in a reactor and the reactor filled with 0.7 M Grignard solution in CPME, heated to 95° C. and left for 20 minutes. After activation of the reaction, 1M PhBr in CPME was flushed through the column at 5 mL/min. An instantaneous reaction was observed causing the magnesium bed to lift. A longer (approx. 7 min.) than theoretical residence time was observed. 5 mL of this solution was collected under nitrogen and 0.51 mL benzaldehyde diluted with 2 mL CPME was added to the flask via syringe. To the resulting brown slurry, 5 mL of 10% $H_2SO_4$ was added to hydrolyze the magnesium salt to the alcohol. The layers were separated and analyzed using GC. The chromatogram (FIG. 4) indicates over 90% conversion of phenyl bromide to diphenyl methanol.

Example 4

Production of a Grignard Reagent Using Cyclopropyl Bromide

Parameters:
Column composition: Metal
Length of column: 106 cm
Inner diameter of column: 1.1 cm
No bulb with larger diameter near top
Volume of column: 100.73 mL
Extra volume (connectors): 3 mL
Pore size frit: 10 μm
Pump: Gilson HPLC pump 50 mL pump head
Tubing from pump: Swagelok 1/16" SS tubing 1 mm ID
Tubing from reactor: Teflon 1/8" tubing 2.4 mm ID 10.1 g (0.42 mol) of 250 μm Mg particles were introduced in a reactor freshly purged with nitrogen and the reactor filled with 1 M PhMgI solution in CPME, heated to 60° C. and left for 60 minutes. After activation of the reaction, the column was cooled to 25° C., and 0.2 M of cyclopropylbromide in CPME was flushed through the column at 5 mL/min. The product was collected under Nitrogen. 20 mL of this solution that was collected was transferred into a flask under inert conditions and 0.307 mL benzaldehyde was added. After solid formation, 20 mL of 1.8 M $H_2SO_4$ was added to hydrolyze the magnesium salt to the alcohol. The layers were separated and the product alcohol was observed to form in high yield without any significant side product formation.

Example 5

Production of a Grignard Reagent Using Synthon A

Parameters:
Column composition: Metal
Length of column: 58 cm
Diameter of column: 1.1 cm
Volume of column: 55 mL
Extra volume (connectors): 3 mL
Pore size frit: 10 μm
Pump: Gilson HPLC pump 10 mL pump head
Refill: 125 ms
Compressibility: 46

10.1 g (0.42 mol) of 250 μm Mg particles were introduced in a reactor and the reactor filled with 1 M MeMgCl solution in THF, heated to 130° C. for 15 minutes. After activation of the reaction, stock solution of synthon A at concentration of 0.592 M in THF was flushed through the column at 5 mL/min at 130° C. Reaction scheme is indicated in Scheme 3a-b above. The first 20 min. fraction was discarded and the product collected under nitrogen. An aliquot of the product was injected on to the GC. The chromatogram (FIG. 6) indicated over 90% conversion of synthon A to its Grignard reagent. 100 mL of this Grignard reagent (56 mmol) was mixed with synthon B (42 mmol) and this mixture was added to a catalyst in a flask. A highly exothermic reaction occurred. The reaction flask was cooled to 25° C. and left to stir overnight. 0.2 N HCl was added to quench the reaction mixture. The layers were separated and analyzed using GC. About 80% yield of the AB ester was obtained.

The invention claimed is:

1. A process of preparing a Grignard reagent comprising the steps of creating a fluid of magnesium particulates and a solvent in a reactor; and contacting the magnesium particulates with at least one organohalide to form the Grignard reagent; wherein the fluid comprises the solvent flowing against gravity through a bed of magnesium particulates ranging in size from 10 to 1000 μm when added, with a flow rate ranging from 0.1 to 0.3 cm/s to create a fluidized bed of magnesium particulates in the solvent.

2. The process of claim 1, wherein the solvent comprises the at least one organohalide.

3. The process according to claim 1, wherein the solvent is a liquid.

4. The process according to claim 1, wherein the solvent is a gas.

5. The process according to claim 1, wherein the particulates range in size from 100 to 500 μm.

6. The process according to claim 5, wherein the particulates range in size from 200 to 400 μm.

7. The process according to claim 2, wherein the solvent further comprises at least one ether solvent.

8. The process according to claim 7, wherein the ether solvent is selected from the group consisting of cyclopentyl methyl ether (CPME), tetrahydrofuran, methyltetrahydrofuran, dioxane and dimethoxyethane.

9. The process according to claim 1, wherein the solvent flows at a rate higher than the settling velocity of the magnesium particulates in at least a part of the process.

10. The process according to claim 1, wherein the flow rate is in the range of 0.1 to 0.2 cm/s in a part of the process where magnesium particulates create the fluidized bed.

11. The process according to claim 1, wherein the magnesium is contained in a reactor column, and wherein a solvent is pumped into the reactor to contact the magnesium, and wherein such contact has a residence time that ranges from 0.1 to 10 minutes.

12. The process according to claim 11, wherein the residence time is in the range from 0.5 to 3 minutes.

13. The process according to claim 11, wherein the reactor is maintained at temperatures in the range of 50° C. to 150° C.

14. The process according to claim 13, wherein the reactor is maintained at a temperature in the range of 75° C. to 125° C.

15. The process according to claim 1, wherein the process is continuous.

16. A continuous process comprising the steps of: creating a fluid of magnesium particulates and a solvent in a reactor column; contacting the magnesium particulates with at least one organohalide to form the Grignard reagent; wherein the fluid comprises the solvent flowing against gravity through a bed of magnesium particulates that range in size from about 10 μm to about 1,000 μm when added, with a flow rate ranging from about 0.1 to about 0.3 cm/s in at least a part of the process to create a fluidized bed of magnesium particulates in the solvent; and contacting the Grignard reagent with a substrate.

17. The process of claim 16, wherein the solvent comprises the at least one organohalide.

18. The process according to claim 16, wherein Grignard reagent flows into contact with the substrate, which is stationary.

19. The process according to claim 18, wherein the fluid of magnesium particulates and solvent continuously replenish Grignard reagent.

20. The process according to claim 16, wherein the solvent is a liquid.

21. The process according to claim 16, wherein the solvent is a gas.

22. The process according to claim 16, wherein the particulates range in size from about 100 to about 500 μm.

23. The process according to claim 16, wherein the particulates range in size from about 200 to about 400 μm.

24. The process according to claim 17, wherein the solvent further comprises at least one ether solvent.

25. The process according to claim 24, wherein the ether solvent is selected from the group consisting of cyclopentyl methyl ether (CPME), tetrahydrofuran, methyltetrahydrofuran, dioxane and dimethoxyethane.

26. The process according to claim 16, wherein the flow rate is in the range of about 0.1 to about 0.2 cm/s in at least a part of the process where magnesium particulates create the fluidized bed.

27. The process according to claim 1, wherein the magnesium is contained in a reactor, and wherein the solvent is introduced into the reactor to contact the magnesium, and wherein such contact has a residence time that is long enough to activate the Grignard reagent.

28. The process according to claim 27, wherein the residence time ranges from 0.1 to 10 minutes.

29. The process according to claim 27, wherein the residence time is in the range from 0.5 to 3 minutes.

30. The process according to claim 27, wherein the reactor is maintained at a temperature in the range of 50° C. to 150° C.

31. The process according to claim 30, wherein the reactor is maintained at a temperature in the range of 75° C. to 125° C.

32. The process according to claim 1, wherein a uniform temperature gradient during preparation of a Grignard reagent is maintained by reacting the magnesium particulates with the organohalide in a fluid bed reactor.

33. The process according to claim 16, wherein a uniform temperature gradient during preparation of a Grignard reagent is maintained by reacting the magnesium particulates with the organohalide in a fluid bed reactor.

34. The process according to claim 4, wherein the gas is methylchloride.

35. The process according to claim 16, wherein the Grignard reagent reacts with a substrate to produce an active drug product.

36. The process of claim 35, wherein the reaction occurs in a microreactor.

37. The process of claim 36, wherein the microreactor may be heated or cooled to yield the active drug product.

38. The process according to claim 16, wherein the magnesium is contained in a reactor, and wherein the solvent is introduced into the reactor to contact the magnesium, and wherein such contact has a residence time that is long enough to activate the Grignard reagent.

* * * * *